United States Patent [19]
Govari et al.

[11] Patent Number: 6,053,873
[45] Date of Patent: Apr. 25, 2000

[54] PRESSURE-SENSING STENT

[75] Inventors: Assaf Govari, Qiryat Haim; Maier Fenster, Petach Tikva, both of Israel

[73] Assignee: Biosense, Inc., Miami, Fla.

[21] Appl. No.: 09/057,634

[22] Filed: Apr. 9, 1998

Related U.S. Application Data

[60] Provisional application No. 60/034,701, Jan. 3, 1997.

[30] Foreign Application Priority Data

Dec. 31, 1997 [WO] WIPO .............................. IL97/00447

[51] Int. Cl.$^7$ .............................. A61B 5/02; A61B 8/14; A61M 29/00
[52] U.S. Cl. .......................... 600/505; 600/462; 600/468; 606/194; 606/191
[58] Field of Search ..................................... 600/505, 462, 600/465, 468, 479, 480; 623/1, 12, 11; 606/191, 194, 198

[56] References Cited

U.S. PATENT DOCUMENTS

| | | | |
|---|---|---|---|
| 4,109,644 | 8/1978 | Kojima | 128/2 V |
| 4,656,463 | 4/1987 | Anders et al. | 340/572 |
| 5,027,107 | 6/1991 | Matsuno et al. | 340/572 |
| 5,073,781 | 12/1991 | Stickelbrocks | 342/51 |
| 5,105,829 | 4/1992 | Fabian et al. | 128/899 |
| 5,205,292 | 4/1993 | Czar et al. | 128/662.03 |
| 5,226,421 | 7/1993 | Frisbie et al. | 600/453 |
| 5,271,410 | 12/1993 | Wolzinger et al. | 600/505 |
| 5,293,399 | 3/1994 | Hefti | 375/7 |
| 5,411,551 | 5/1995 | Winston et al. | 623/1 |
| 5,483,826 | 1/1996 | Schultz et al. | 73/146.5 |
| 5,497,147 | 3/1996 | Arms et al. | 340/870.35 |
| 5,522,394 | 6/1996 | Zurbrugg | 128/662.06 |
| 5,873,835 | 2/1999 | Hastings et al. | 600/488 |

OTHER PUBLICATIONS

Ultrasonic System for Noninvasive Measurement of Hemodynamic Parameters of Human Arterial–Vascular System, Powaloski, T., Archives of Acoustics, vol. 13, Issue 1–2, pp. 89–108 (1988).

"A Noninvasive Ultrasonic Method for Vascular Input Impedance Determination Applied in Diagnosis of the Carotid Arteries", Powalowski, T., Archives of Acoustics, vol. 14, Isue 3–4, pp 293–312 (1989).

Bio–Medical Telemetry, Sensing and Transmitting Biological Information from Animals and Man, Second Edition, Mackay, R. Stuart, IEEE Press (1993) p. 111–147.

Archives of Acoustics, "Ultrasonic System for Noninvasive Measurement of Hemodynamic Parameters of Human Arterial–Vascular System", Powalowski T., vol. 13, Issue 1–2, p. 89–108 (1988).

Archives of Acoustics, "A Noninvasive Ultrasonic Method for Vascular Input Impedance Determination Applied in Diagnosis of the Carotid Arteries", Powalowski T., vol. 14, Issue 3–4, pp. 293–312 (1989).

Proceedings of the Conference on Ultrasonics in Biology and Medicine, UBIMED–70, "The Transcutaneous Ultrasonic Flow–Velocity Meter in the Study of Arterial Blood Velocity", J.P. Woodcock, Jablonna–Warsaw, Oct. 5–10, (1970).

Primary Examiner—Max Hindenburg
Assistant Examiner—Navin Natnithithadha
Attorney, Agent, or Firm—Paul A. Coletti; Louis J. Capezzuto

[57] ABSTRACT

Implantable apparatus for measuring a fluid flow in the body of a subject, including a stent, having a generally cylindrical radial outer wall and a central lumen. A flow parameter sensor is fixed to the stent, and measures a parameter relating to a rate of blood flow through the stent. A transmitter transmits signals responsive to the measured parameter to a receiver outside the body.

24 Claims, 6 Drawing Sheets

FIG. 9

PRESSURE-SENSING STENT

RELATED APPLICATIONS

This application claims priority from PCT application Ser. No. IL97/00447 filed Dec. 31, 1997. Application Ser. No. IL97/00447 itself claims priority from U.S. Provisional application Ser. No. 60/034,701, filed Jan. 3, 1997. Both applications are signed to the Assignee of the present patent application, and both applications are incorporated herein by reference.

FIELD OF THE INVENTION

The present invention relates to the field of vascular measurement, and in particular to measuring parameters relating to blood flow through a vascular stent.

BACKGROUND OF THE INVENTION

Atherosclerosis, narrowing of the blood vessels, is a common disease of advancing age. When important vessels narrow beyond a certain limit, damage to major organs of the human body may occur, for example, heart attacks and strokes. In addition, organs that have a chronically impaired blood supply do not function properly, leading in many cases to debilitating illnesses.

One of the most common treatments for narrowed blood vessels is angioplasty. During an angioplasty procedure, a balloon is inserted into the narrowed portion of the blood vessel and inflated, thereby widening the lumen. In a supplementary technique, a stent is inserted into the blood vessel at the widened location to support the vessel (which may have been damaged by the angioplasty) and to maintain an open lumen. In extreme cases a portion of the circulatory system may be replaced with a tissue graft or with a graft manufactured of biocompatible materials. Newer stents are radio-opaque, and are visible under fluoroscopy, which aids in guiding them into position.

It frequently occurs, however, that the blood vessel narrows again after the procedure, either by accumulation of plaque or other material inside the stent or graft, or by (unrelated) narrowing of the blood vessel at other locations. Thus, in many cases, an angioplasty procedure must be repeated after a time, or bypass surgery must be performed on the patient. It would be desirable to monitor the flow of blood inside the stent or graft, so as to determine whether significant narrowing has occurred.

Various methods of measuring flow velocities and volumes are known in the art, including ultrasonic and electromagnetic sensors. For example, U.S. Pat. No. 5,522,394, the disclosure of which is incorporated herein by reference, describes an implantable probe for measuring blood flow velocity. U.S. Pat. No. 5,205,292, the disclosure of which is incorporated herein by reference, describes an implantable probe for measuring blood flow velocity and other physiological parameters, which is attached to the outside of a blood vessel. U.S. Pat. No. 4,109,644, the disclosure of which is incorporated herein by reference, describes an implantable wireless ultrasound probe which is powered by external electromagnetic induction and transmits outside the body, via electromagnetic radiation, a signal indicative of ultrasound signals received by the probe.

In Doppler ultrasound, the flow is irradiated with ultrasonic waves at a given frequency. The reflection of the ultrasound from the flow is shifted by the Doppler effect to a different frequency from the transmitted frequency. Since the Doppler shift is linearly related to the flow velocity, the velocity can be determined by analyzing the frequency spectrum of the reflection.

Another type of ultrasound flow meter is the transit time flow meters, which takes advantage of a difference in propagation velocity between upstream propagation and downstream propagation of ultrasound waves. Waves traveling in the direction of flow move faster than waves which travel in a direction opposite the flow.

Electromagnetic flow meters (EMF) use the well-known property that a voltage potential develops across a conductor moving in a magnetic field. To generate an EMF in a blood vessel, it is surrounded by an induction coil, which generates a magnetic field on the blood vessel. The voltage that develops on the blood is measured on the blood vessel rather than on the blood.

Miniature transmitters, suitable for implantation in the human body for transmission of physiological parameters are well known in the art.

"Bio-Medical Telemetry (second edition)", by R. S. Mackay, published by the IEEE press, 1993, the disclosure of which is incorporated herein by reference, describes several types of miniature transmitters, which transmit measurements from implanted physiological sensors to receivers outside the body. In particular, Mackay, in chapter 5, pp. 111–147 describes pressure sensors for measuring various physiological parameters, including blood pressure. On page 143, Mackay describes a variable inductance pressure sensor which is attached to the outside of a vessel. The sensor includes a transmitter, which includes a coil coupled to the pressure sensor, such that a ferrite moves axially within the coil in response to changes in pressure, so as to cause a variation in the inductance of the coil and frequency-modulate the radiation that the coil transmits. such a transmitter is also described in U.S. Pat. No. 5,497,147, the disclosure of which is incorporated herein by reference.

On page 138, Mackay suggests placing a pressure sensor into the vascular system, such as into an artificial heart valve, but recommends against placing a pressure sensor inside the blood stream due to the obstruction caused by the pressure sensor and by the danger of forming blood clots. It is however known to place pressure sensors into the blood stream to directly measure pressure, for example, in a study described on page 331 of Mackay in which a pressure sensor was inserted into an aorta of a baboon. It is also known to use intra-vascular pressure sensors to control demand responsive pacemakers.

Chapter 10 of Mackay, pp. 298–315, describes various methods of passive transmission, wherein the energy for sensing and transmission is provided by an outside source. In particular, a transmitter using a tunnel diode, two capacitors and a coil is described, in which one capacitor stores energy during a charging phase and releases the energy to an oscillator which includes the other capacitor, the coil and the tunnel diode. The transmitted frequency is offset from the received frequency.

Use of flow of blood in a magnetic field to generate power for an implantable device, is described on page 70 of Mackay, and is suggested as being suitable only in large blood vessels. Using the voltage generated by such a flow for an implantable flowmeter is not suggested by Mackay.

U.S. Pat. No. 4,656,463, the disclosure of which is incorporated herein by reference, describes a LIMIS (Location Identification, measuring of Movement of Inventory System) which uses miniature coded transponders.

U.S. Pat. Nos. 5,073,781, 5,027,107 and 5,293,399, the disclosures of which are incorporated herein by reference, describe miniature transponders having no internal power supply.

U.S. Pat. No. 5,483,826, the disclosure of which is incorporated herein by reference, describes a miniature transponder for transmitting pressure values of a vessel, such as a tire.

U.S. Pat. No. 5,105,829, the disclosure of which is incorporated herein by reference, describes a passive transmitter which is adapted for implantation into the human body and which is capacitively coupled to the body to better transmit a signal indicative of a foreign object left in the body during a surgical procedure.

SUMMARY OF THE INVENTION

It is an object of the present invention to provide a stent, which measures parameters relating to flow of a fluid therethrough, and/or parameters relating to possible occlusion of the flow, and transmits the measurement results to a receiver outside the body.

In one aspect of the present invention, the stent is implanted in a blood vessel of a subject.

In another aspect of the present invention, the stent includes no active power source, such as a battery, but rather receives power from an externally applied electromagnetic field.

In preferred embodiments of the present invention, a stent, for implantation in a blood vessel in the body of a subject, comprises a flow parameter sensor and a transmitter. The flow parameter sensor measures a rate of flow of blood through the vessel, and the transmitter transmits signals responsive to the flow parameter sensor's measurement. Preferably, the signals are received and analyzed by a receiver outside the body, either continuously or intermittently, to determine whether flow through the vessel is occluded and, if so, to what extent.

In some preferred embodiments of the present invention, the flow parameter sensor and transmitter are powered by a battery, which is preferably mechanically fixed to the stent. The battery is preferably a primary battery, of a type known in the art. Alternatively, the battery may be a rechargeable battery, and the stent may further have recharging circuitry associated therewith, for example, inductively-coupled recharging circuitry, as is known in the art.

In other preferred embodiments of the present invention, the flow parameter sensor and transmitter are powered by electrical energy received from a source outside the body, and are active only when a suitable source of such energy is brought into proximity with the body.

In some of these preferred embodiments, the stent comprises a resilient coil, made of electrically-conductive material and coupled at both ends to circuitry associated with the flow parameter sensor and/or the transmitter. The energy source outside the body generates a time-varying magnetic field in a vicinity of the coil, which field is preferably generally aligned with a central axis thereof, thus causing an electrical current to flow in the coil and provide energy to the flow parameter sensor and/or transmitter.

In some preferred embodiments of the present invention, the flow parameter sensor comprises an electromagnetic sensor. A magnetic field, preferably a DC magnetic field in a direction generally perpendicular to the long axis of the stent, is applied to the stent by a magnetic field generator outside the body. This magnetic field causes an magnetohydrodynamic electrical potential to develop across the stent, proportional to the rate of flow of the blood therethrough, which potential is measured by the flow parameter sensor. Preferably, the stent comprises only non-magnetic materials, so as not to distort the lines of magnetic field. Alternatively, the stent comprises ferro-magnetic materials which concentrate the magnetic filed at a region adjacent electrodes which measure the induced potential. It should be noted that magnets are generally undesirable in a stent as they may cause damage to local tissues by the chronic presence of an induced potential.

In other preferred embodiments of the present invention, the flow parameter sensor comprises at least one pressure sensor, which generates signals responsive to pulsatile pressure changes in the blood vessel due to beating of the subject's heart. The relative pulsatile pressure change generally increases immediately upstream of a constriction in the blood vessel or within the stent. "Ultrasonic System for Noninvasive Measurement of Hemodynamic Parameters of Human Arterial-Vascular System", by Powalowski T., ARCHIVES OF ACOUSTICS, Vol. 13, Issue 1-2, pp. 89–108 (1988) and in "A Noninvasive Ultrasonic Method for Vascular Input Impedance Determination Applied in Diagnosis of the Carotid Arteries", by Powalowski T., ARCHIVES OF ACOUSTICS, Vol. 14, Issue 3-4, pp. 293–312 (1989), the disclosures of which are incorporated herein by reference, describe a method of estimating instantaneous blood pressure in a blood vessel using ultrasound (external to the body). In addition, a method of estimating a constriction and the general condition of a vascular system is described in these article and in Woodcock, J. P., "The Transcutaneous Ultrasonic Flow-Velocity Meter in the Study of Arterial Blood Velocity," Proceedings of the Conference on Ultrasonics in Biology and Medicine, UBIMED-70, Jablonna-Warsaw, Oct. 5–10, 1970.

The Woodcock article describes a method for assessing collateral circulation by analyzing two, spaced apart, flow measurements. In a preferred embodiment of the present invention, this is achieved using two spaced apart implanted stents and a single controller which receives signals indicative of flow from both stents.

Preferably, the at least one pressure sensor comprises at least two such sensors, arrayed along the length of the stent. Any significant variation in the pulsatile pressure change from one of the sensors to another is generally indicative of a constriction in the stent.

In some preferred embodiments of this type, the at least one pressure sensor comprises a pressure-to-frequency transducer. This transducer preferably comprises a flexible, resilient diaphragm fixed within a radial outer wall of the stent, so that the diaphragm expands radially outward in response to pressure increases within the stent and can also contract inward when the pressure in the stent decreases. The diaphragm is circumferentially surrounded by an electrical coil, fixed to the wall or contained within the wall material, which coil forms a part of a resonant circuit. A magnetic core, preferably a ferrite, is fixed to the diaphragm, so that when the diaphragm expands or contracts, the core is displaced relative to the coil, thus varying the inductance of the coil in proportion to the pressure within the stent.

In operation, a time-varying electromagnetic excitation field is generated in a vicinity of the stent, preferably by a field generator, such as a coil, external to the body. The field, which preferably has a frequency at or near a resonant frequency of the resonant circuit, causes an electrical current to flow in the coil and thus in the resonant circuit. The coil radiates an electromagnetic response field having a variable characteristic, such as a phase shift or decay frequency relative to the excitation field, dependent on the varying inductance of the coil. The response field is detected by a receiver outside the body, which analyzes the variable characteristic thereof to measure changes of pressure within the stent.

In one preferred embodiment of this type, the resonant circuit comprises a tunnel diode and a capacitor, coupled in series with the coil. The coil, tunnel diode and capacitor are preferably fixed to an outer surface of the stent and interconnected using surface-mounted printed circuit technology. The excitation field is alternately switched on and off, preferably in a square wave pattern. The response field will rise and fall in response to the square wave pattern, wherein the fall of the response field will have a characteristic, variable frequency dependent on the variable inductance of the coil.

It will be appreciated that in preferred embodiments of this type, the resonant circuit, including the coil and diaphragm-mounted core, constitutes both the flow parameter sensor and the transmitter of the present invention. The resonant circuit receives electrical power from the excitation field, without the need for a power source to be implanted with the stent.

Alternatively, in other preferred embodiments of the present invention, the at least one pressure sensor may comprise a pressure sensor of any suitable type known in the art, for example, a piezoelectric pressure transducer. The transmitter may comprise any suitable miniature, implantable transmitter circuit known in the art.

In still other preferred embodiments of the present invention, the flow parameter sensor comprises one or more ultrasound-responsive devices, positioned along the length of or, preferably, at the ends of the stent.

In some preferred embodiments of this type, the flow parameter sensor comprises a transit-time sensor, wherein the ultrasound-responsive devices comprise a pair of ultrasound transducers, positioned at opposite ends of the stent. A first one of the transducers, at the upstream end of the stent, is driven to emit ultrasound signals into the blood stream flowing through the stent. These signals are detected by the second transducer, at the downstream end of the stent, and the downstream transit time, from the first to the second transducer, is measured. Similarly, the second transducer is driven to emit ultrasound signals, the first transducer detects them, and the upstream transit time, from the second to the first transducer, is measured. As is known in the art, the difference between the upstream and downstream transit times is generally proportional to the speed of blood flow through the stent. The speed of blood flow will generally vary according to a pulsatile waveform, synchronized with the beating of the heart. Changes in this waveform may be indicative of an occlusion in or near the stent.

In other preferred embodiments of this type, the flow parameter sensor comprises a Doppler flow meter. The ultrasound-responsive devices preferably comprise a miniature Doppler ultrasound transducer, which is fixed to the stent and generates frequency-shift signals indicative of blood velocity in the stent.

Alternatively, the Doppler measurement may be made using a Doppler ultrasound system outside the body, preferably a Doppler imaging system, as is known in the art. In this case, the stent is preferably acoustically matched to the blood and the blood vessel, so that it does not impede the progress of the ultrasound system. Alternatively, only a portion of the stent is made transparent to ultrasound. Alternatively, the Doppler system is aimed at a location adjacent the stent, preferably, based on an image or on reflections from the stent. The ultrasound-responsive devices associated with the stent comprise ultrasound transponders or other ultrasound markers, known in the art, such as air-filled bubbles. Preferably two such devices are positioned at opposite ends of the stent or fixed to the blood vessel, one upstream and one downstream from the stent, at suitable, known distances therefrom. The Doppler ultrasound system detects the positions of the devices, thereby defining precisely the location and orientation of the stent. The position and orientation thus defined are used in optimally aiming a transducer of the Doppler system with respect to the stent to maximize the Doppler signal therefrom and/or to correct the Doppler measurements for the angle thus determined of the transducer relative to the stent.

In further preferred embodiments of the present invention, the flow parameter sensor comprises a bioimpedance measurement device. This device comprises at least one pair of electrodes, at mutually-opposing radial positions along the length of the stent. Each such pair of electrodes is used to measure electrical impedance, as is known in the art, across a diameter of the stent at the axial position of the pair. As blood generally has substantially lower impedance than does plaque, an occlusion of the stent at or adjacent to the axial position of the pair will generally cause the impedance between the pair to increase. Thus, changes in impedance between one pair of electrodes and/or substantial variations in impedance between two such pairs at different axial positions along the stent may be indicative of occlusion of the stent.

In some preferred embodiments of the present invention, the stent also includes sensors of other types known in the art, for example, pH and other chemical sensors, temperature sensors and oxygen saturation sensors. Preferably, these sensors are fabricated on or in the stent or on a preferably flexible thin film attached to the stent, more preferably using silicon microcircuit technology.

As described above with regard to several of the preferred embodiments of the present invention, flow measurements made by the flow parameter sensor involve receiving and analyzing pulsatile flow-responsive signals, such as pressure signals, which are synchronized with the heart beat. Therefore, when such signals are to be received from the stent, the subject's ECG is preferably monitored, as well, in order to give a baseline synchronization signal. The ECG signal is useful in identifying the time of diastole, in order to calibrate the flow-responsive signals to the minimal or near-zero flow at this time. The ECG can also be used in determining a range of motion of the stent, relative to an eternally-applied RF or magnetic field, due to the movement of the heart as it beats.

Furthermore, in some abnormal heart conditions, blood flow in the coronary arteries is not properly synchronized with the heart beat, resulting in low perfusion of the heart tissue. The ECG can be taken together with the flow-responsive signals from the stent to identify and diagnose such conditions.

Although the preferred embodiments described herein make reference to arterial stents, it will be appreciated that principles of the present invention may generally be applied to other types of stents, such as urinary stents for implantation in the urethra, as well as to other implantable flow-through devices, such as implantable cardiac-assist pumps.

There is therefore provided in accordance with a preferred embodiment of the invention, implantable apparatus for measuring a fluid flow in the body of a subject, including:

a stent, having a generally cylindrical radial outer wall and a central lumen;

a flow parameter sensor fixed to the stent, which measures a parameter relating to a rate of blood flow through the stent; and a transmitter, which transmits signals responsive to the measured parameter to a receiver outside the body. Preferably, the flow parameter sensor includes a pair of electrodes, in communication with the lumen. Preferably, the electrodes are placed in radially-opposing positions along the outer wall.

Alternatively or additionally, the flow parameter sensor measures a magnetohydrodynamic potential across the lumen. Alternatively or additionally, the flow parameter sensor measures an electrical impedance across the lumen.

Alternatively or additionally, the flow parameter sensor includes at least one pressure sensor. Preferably, the at least one pressure sensor includes a plurality of pressure sensors along the length of the stent. Alternatively or additionally, the pressure sensor includes a pressure-to-frequency transducer.

Preferably, the flow parameter sensor includes at least one ultrasound-responsive device. Preferably, the at least one ultrasound-responsive device includes two ultrasound transducers, each fixed in a known relation to a respective end of the stent. Preferably, the two ultrasound transducers function as ultrasound transponders.

Alternatively or additionally, the flow parameter sensor measures a transit time of ultrasound signals through the stent. Alternatively or additionally, the flow parameter sensor measures a Doppler shift of ultrasound signals reflected from a fluid flowing in the lumen.

Preferably, the transmitter further receives energy from an electromagnetic field, and supplies the energy to the flow parameter sensor. Alternatively or additionally, the transmitter includes a coil fixed to the stent. Preferably, the coil is helically-disposed within the outer wall of the stent, along the length thereof. Alternatively or additionally, the coil includes resilient material.

Preferably, the flow parameter sensor includes:

a flexible diaphragm, fixed within the outer wall of the stent so as to expand radially outward in response to a pressure increase in the lumen; and a deflection sensor, which generates signals responsive to expansion of the diaphragm. Preferably, the deflection sensor includes:

a magnetic core fixed to the diaphragm; and an electrical coil, circumferentially surrounding the diaphragm and the coil, so that movement of the core due to expansion of the diaphragm causes a change in the inductance of the coil, responsive to the pressure increase. Preferably, the transmitter includes:

the electrical coil; and circuitry coupled to the coil, having a resonant frequency dependent on the inductance of the coil, where the coil receives energy from an electromagnetic field and radiates energy substantially at the resonant frequency.

In a preferred embodiment of the invention, the apparatus includes an implantable capsule, which supplies energy to the flow parameter sensor. Preferably, the capsule contains the transmitter. Alternatively or additionally, the apparatus includes memory circuitry within the capsule, for storing measurements made by the flow parameter sensor.

There is also provided in accordance with a preferred embodiment of the invention a method for measuring blood flow in the body of a subject, including:

implanting a stent, to which a transmitter is coupled, in a blood vessel in the body; and receiving signals from the transmitter, responsive to blood flow through the stent. Preferably, the method includes irradiating the body with an electromagnetic field, to provide energy to the stent. Alternatively or additionally, the method includes receiving an ECG signal from the subject, and using the ECG signal in analyzing the blood flow signals received from the transmitter. Alternatively or additionally, the method includes applying a magnetic field to the body in a vicinity of the stent, in a direction generally transverse to the flow of blood through the stent; and measuring an electrical potential across the stent, along a transverse axis thereof generally perpendicular to the direction of the magnetic field, where receiving signals from the transmitter includes receiving signals responsive to the electrical potential.

Alternatively or additionally, the method includes measuring a bioimpedance across the stent, wherein receiving signals from the transmitter includes receiving signals responsive to the bioimpedance. Alternatively or additionally, the method includes measuring a pressure in the stent, wherein receiving signals from the transmitter includes receiving signals responsive to the pressure.

Additionally or alternatively, the method includes detecting ultrasonic signals from blood flowing in the stent, wherein receiving signals from the transmitter includes receiving signals responsive to the detected ultrasonic signals. Preferably, detecting ultrasonic signals includes measuring a transit time of ultrasound waves passing through the stent. Alternatively or additionally, detecting ultrasonic signals includes measuring a Doppler shift of ultrasound waves reflected from the blood.

There is also provided in accordance with a preferred embodiment of the invention a method for measuring blood flow in a stent implanted in a blood vessel in the body of a subject, including:

implanting two ultrasound markers along the blood vessel, each marker in a known spatial relation to a respective end of the stent;

determining respective positions of the markers relative to an ultrasound probe;

aligning the probe with a long axis of the stent using the determined positions of the markers; and receiving and analyzing Doppler ultrasound signals from blood flowing in the stent.

Preferably, implanting the two ultrasound markers includes fixing the markers to the stent. Alternatively or additionally, implanting the two markers includes implanting two ultrasound transponders. Alternatively or additionally, implanting the two markers includes implanting two ultrasound frequency doublers. Alternatively or additionally, determining the positions of the markers includes forming an ultrasound image of a portion of the body that contains the stent.

There is provided in accordance with another preferred embodiment of the invention a method for fabricating a stent, including:

forming at least a portion of the stent from non-conducting material;

fixing electronic components to the portion; and printing strips of conducting material on a surface of the portion to interconnect the components. Preferably, the non-conducting materials include polyimide plastic. Additionally or alternatively, printing the strips on the surface includes transferring an image of the strips to the surface by photolithography.

There is provided in accordance with another preferred embodiment of the invention, an implantable stent made in the above described manner.

The present invention will be more fully understood from the following detailed description of the preferred embodiments thereof, taken together with the drawings in which:

DETAILED DESCRIPTION OF PREFERRED EMBODIMENTS

Figure 1A:
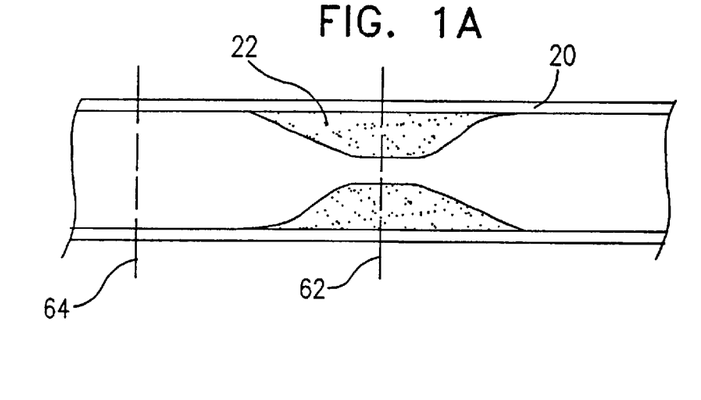
FIG. 1A is a schematic, sectional illustration of a blood vessel, partly occluded by a stenosis.

Reference is now made to FIG. 1A, which is a schematic, sectional illustration of a blood vessel 20, generally an artery, which is partially occluded by a stenosis 22. As is known in the art, such stenoses are commonly treated by percutaneously inserting and inflating a balloon at the tip of a catheter (not shown in the figures) at the point of stenosis 22, so as to expand vessel 20 approximately back to its normal diameter. Other methods of angioplasty, known in the art, may also be used for this purpose.

Figure 1B:
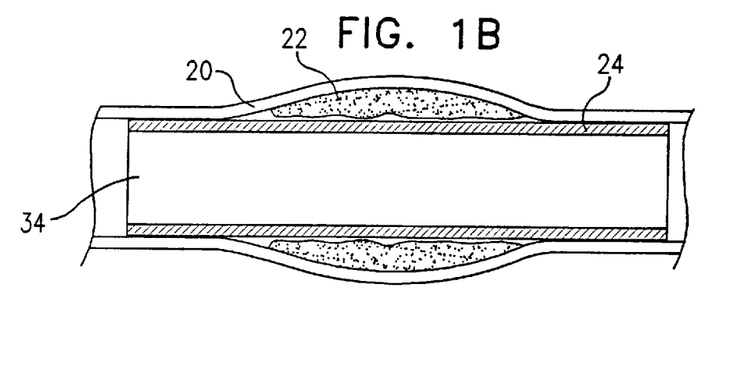
FIG. 1B is a schematic, sectional illustration showing a stent, in accordance with a preferred embodiment of the present invention, implanted in the blood vessel of FIG. 1A.

As shown in FIG. 1B, after vessel 20 has been expanded, a stent 24 is implanted in the vessel at the location of stenosis 22. Stent 24 is preferably implanted in vessel 20 by inserting the stent percutaneously and passing it through the vascular system with the assistance of a suitable catheter, as is known in the art. Alternatively, the stent may be implanted surgically, for example, during open heart surgery.

In accordance with preferred embodiments of the present invention to be described below, stent 24 includes a flow parameter sensor, for sensing blood flow through the stent, and a transmitter, for transmitting signals from the flow parameter sensor to a receiver outside the body of a subject in whose blood vessel 20 stent 24 has been implanted. Stent 24 preferably comprises non-conducting, non-magnetic, biocompatible, plastic material, such as polyimide, as is well known in the art.

Figure 2:
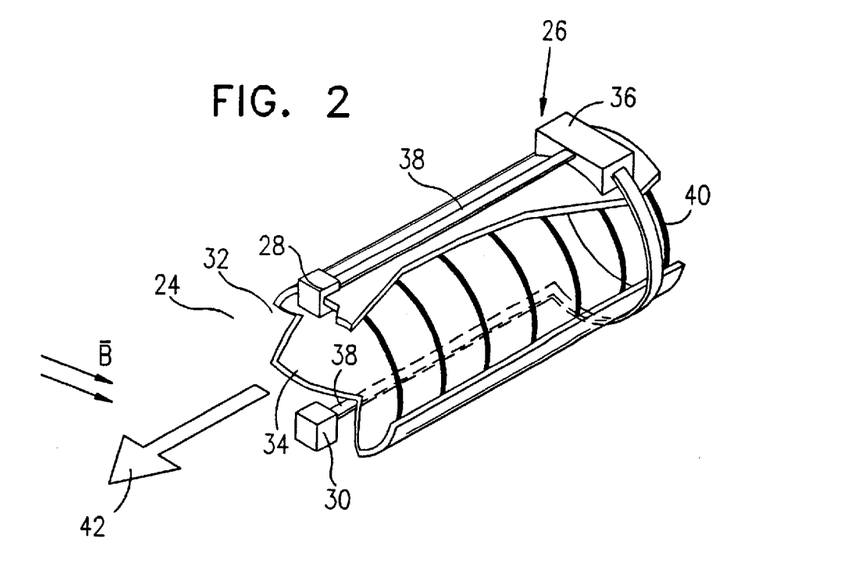
FIG. 2 is a schematic, partially cutaway illustration of a stent including an electromagnetic flow sensor, in accordance with a preferred embodiment of the present invention.

FIG. 2 schematically illustrates, in cutaway view, a preferred embodiment of the present invention in which stent 24 includes circuitry 26 for electromagnetic measurement and transmission of blood flow. Stent circuitry 26 includes a pair of electrodes 28 and 30, opposingly situated on or within radial wall 32 of stent 24. Electrodes 28 and 30 are in electrical contact with blood passing through lumen 34 of stent 24, as illustrated particularly with regard to electrode 30. Circuitry 26 further includes a modulator 36, which is coupled to electrodes 28 and 30, preferably via printed wiring lines 38, which are printed onto radial wall 32 using photolithography processes known in the art.

Preferably, circuitry 26 further includes a helical coil 40, which is electrically coupled to modulator 36. Preferably, modulator 36 comprises a frequency modulator. Coil 40 acts as an antenna to receive RF energy from an external source and to transmit modulated RF signals to an external receiver, as will be described below. The coil comprises resilient, electrically conductive material, such as medical-grade, preferably non-magnetic stainless steel, electrically insulated from the blood in lumen 34. Thus, coil 40 serves both as the receiving/transmitting antenna for circuitry 26 and as a mechanical strengthening element for stent 24. More preferably, coil 40 may comprise a shape memory material, such as Nitinol, which enables stent 24 to be radially collapsed during insertion into vessel 20 and expanded when in place, as is known in the art.

In order to measure the rate of blood flow through stent 24, a magnetic field, $\vec{B}$, preferably a DC magnetic field, is applied to the area of the stent in the subject's body. As illustrated in FIG. 2, the magnetic field is applied in a direction transverse to the blood flow through the stent, indicated by arrow 42, and generally perpendicular to an axis defined by electrodes 28 and 30. This magnetic field causes a potential difference to develop and an electrical current to flow between electrodes 28 and 30, proportional to the blood flow rate. This potential difference or current is received by modulator 36, which modulates the signal transmitted by coil 40 so as to transmit information regarding this potential difference to a receiver outside the body, as will be described below.

Figure 3:
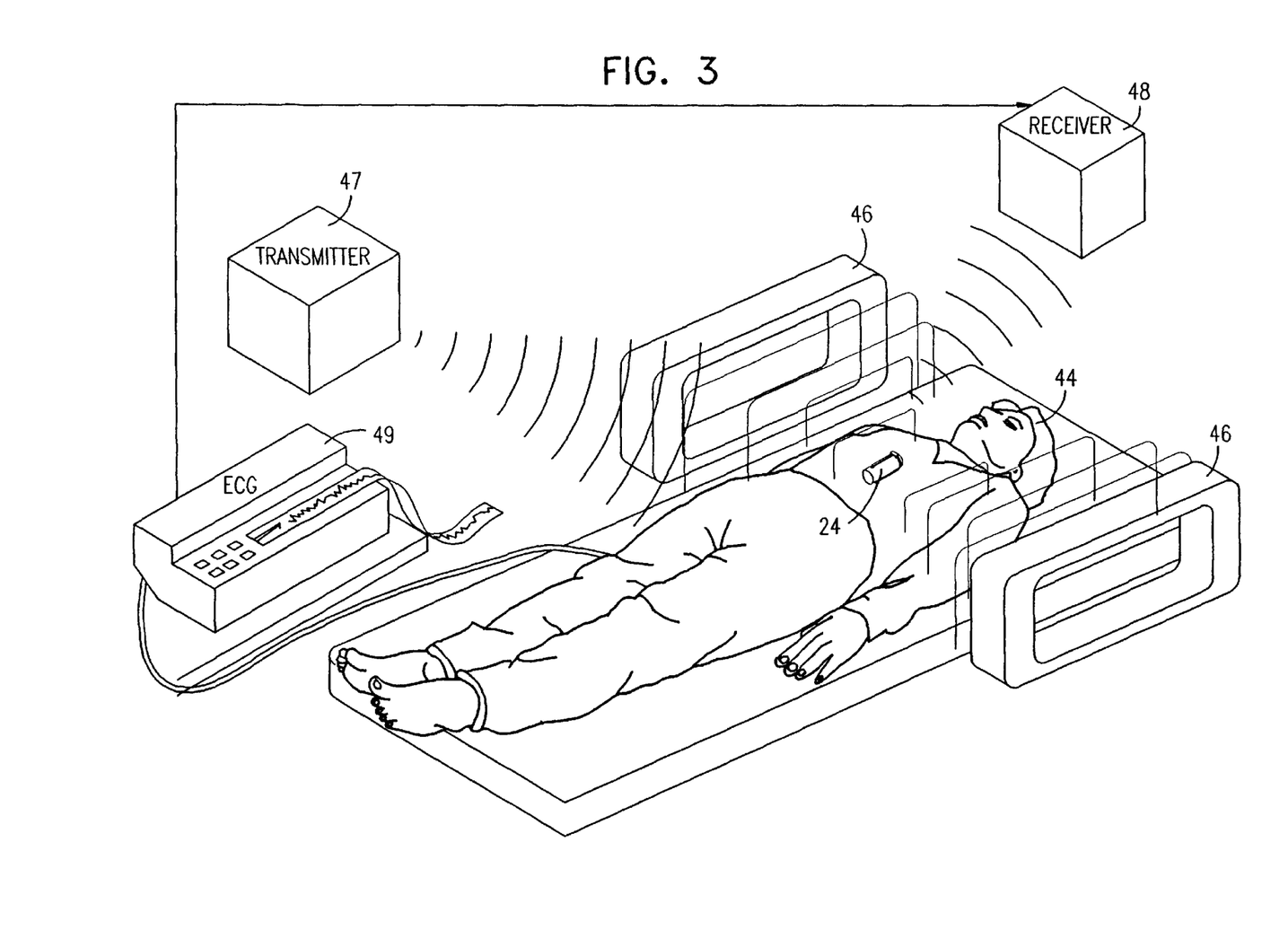
FIG. 3 is a schematic illustration showing a system useful in receiving and analyzing signals responsive to blood flow through the stent of FIG. 2, which is implanted in a blood vessel of a subject, in accordance with a preferred embodiment of the present invention.

FIG. 3 is a schematic illustration showing a system for measuring the rate of blood flow through stent 24, which is implanted in a blood vessel of a subject 44. A pair of DC magnets 46, for example, Helmholtz coils, produce the magnetic field $\vec{B}$ shown in FIG. 2. Preferably, the magnetic field generated by magnets 46 has substantially constant field strength of at least 0.1 T in the region of the subject's body, so that the proportionality of the current flowing between electrodes 28 and 30 to the blood flow rate is substantially unaffected by lateral movement of the subject within the region. $V = \vec{B} vl$, where v is the velocity of the blood and l is the distance between the electrodes. Potential V develops at a direction orthogonal to $\vec{B}$ and v. Preferably, each time the blood flow through stent 24 is measured, the magnetic field and subject 44 are mutually aligned so that the potential or current measured between electrodes 28 and 30 is maximized. These maximum flow measurements are compared with previous maximum flow measurements, in order to eliminate or at least reduce variations in flow readings due to variations in the angular orientation of stent 24 relative to the field.

Alternatively, magnets 46 may be AC magnets, producing a time-varying magnetic field $\vec{B}$. In this case, the potential or current measured between electrodes 28 and 30 will have a similar time variation to that of the field. This time variation may be used, as is known in the art, in phase-sensitive detection and analysis of the signal, so as to reduce noise and compensate for movement during the flow measurement.

A transmitter 47 transmits an RF electromagnetic field, which is received by coil 40 in the stent and provides electrical energy to circuitry 26, as described above. The modulated signal transmitted by the coil is received by a receiver 48, which demodulates and analyzes the signal to determine the rate of blood flow.

In general, the rate of blood flood in stent 24 will not be constant, particularly when blood vessel 20 in which the stent is implanted is an artery, but will rather increase and decrease in pulsatile fashion, in response to the beating of the subject's heart. Therefore, as shown in FIG. 3, an ECG monitor 49 preferably detects the ECG of subject 44 while the blood flow rate is being measured, and ECG data are conveyed from monitor 49 to receiver 48. These data enable the receiver to more readily detect the pulsatile increase and decrease in the modulation of the signal transmitted by coil 40 and thus more accurately determine the blood flow rate.

The ECG signals are preferably also used to identify the time of diastole, so that a minimum or zero-flow baseline measurement may be made at this time. Such measurements are preferably made and recorded over an extended period, in order to detect any drift in the baseline.

Figure 4A:
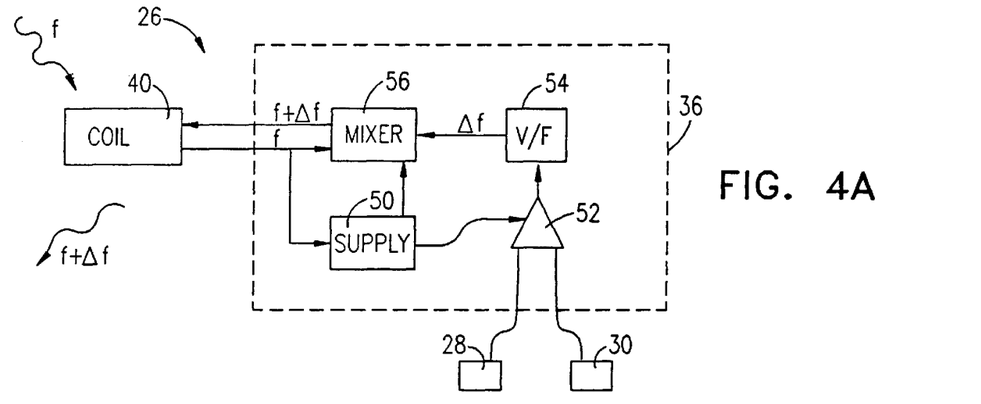
FIG. 4A is an electronic block diagram, schematically illustrating circuitry associated with the stent of FIG. 2, in accordance with a preferred embodiment of the present invention.

FIG. 4A is an electrical block diagram illustrating elements and principles of operation of circuitry 26 described above, in accordance with a preferred embodiment of the present invention. Coil 40 receives energy from an external RF field at a frequency f, causing a current to flow between coil 40 and modulator 36. The modulator includes a power supply 50, which receives and rectifies a portion of the current flowing from the coil, so as to provide power to a preamplifier 52 and a mixer 56. Electrodes 28 and 30 are coupled to the inputs of preamplifier 52, which amplifies a potential difference or a current signal generated in response to blood flow in lumen 34 between the electrodes.

The amplified signal from preamplifier 52 is fed to a voltage-to-frequency converter 54, which generates a modulation frequency Δf, responsive to the electrode signal. Preferably, converter 54 generates a non-zero baseline frequency even when the potential difference between electrodes 28 and 30 is substantially zero, so that receiver 48 will be able to receive and measure at least a baseline signal whenever stent 24 is in the vicinity of transmitter 47 and receiver 48. The modulation frequency Δf is fed back to mixer 56, which receives the current at frequency f from coil 40 and outputs a modulated current at frequency f+Δf back to the coil. The coil re-radiates a field at frequency f+Δ, which is received and demodulated by an external receiver.

Although modulator 36 as shown in FIG. 4A (as well as in FIG. 4B, to be described below) is a frequency modulator, other types of modulators, known in the art, may be used in its stead, for example, phase modulators, amplitude modulators and pulse width modulators. If modulator 36 comprises an amplitude modulator, it preferably operates by coded amplitude modulation, so as to avoid erroneous readings due to spurious amplitude variations, for example, resulting from variations in the orientation of stent 24 relative to receiver 48.

Preferably, the components of modulator 36 are fabricated using microcircuit technology, as is known in the art. More preferably, modulator 36 comprises a single, custom-designed integrated circuit. Further preferably, modulator 36 or its components are assembled on a flexible thin film printed circuit, which is preferably encapsulated in or on surface 32 of stent 24.

It will be understood that FIG. 4A represents a simplified, schematic design, and that other suitable circuit designs, known in the art, may be used instead. Specifically, although modulator 36 is shown and described as a frequency modulator, other modulation schemes known in the art may also be used, for example, amplitude, phase or pulse-width modulation.

Figure 4B:
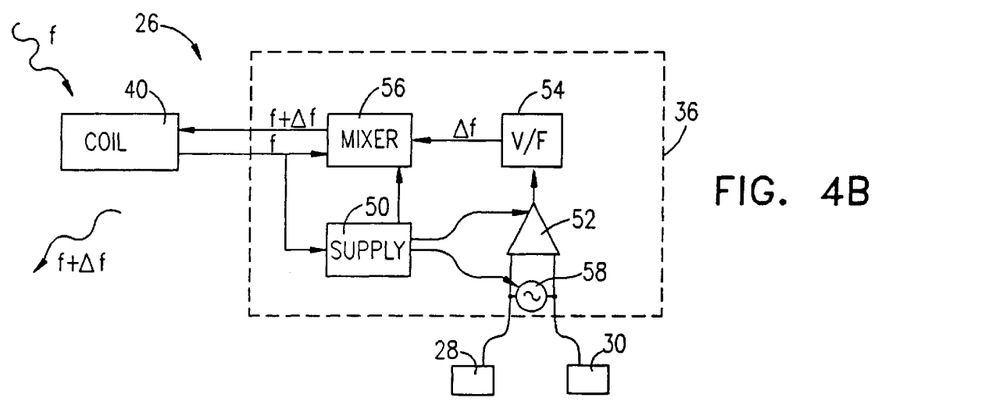
FIG. 4B is an electronic block diagram, schematically illustrating circuitry associated with the stent of FIG. 2, in accordance with an alternative preferred embodiment of the present invention.

FIG. 4B is an electrical block diagram illustrating circuitry 26 in accordance with an alternative preferred embodiment of the present invention, in which electrodes 28 and 30 are used to detect bioimpedance across blood vessel 20, rather than magnetic-field-induced current or potential, as was described above. The elements of circuitry 26 shown in FIG. 4B are generally the same as those shown in FIG. 4A, except that in FIG. 4B modulator 36 includes a constant-amplitude, preferably AC current source 58, connected between electrodes 28 and 30. The current source, which receives power from rectifier 50, causes a potential to develop between the electrodes proportional to an electrical impedance therebetween, in accordance with Ohm's law, i.e., at constant-amplitude current, the resultant amplitude of the potential gives a direct measure of the impedance. This potential is amplified by preamplifier 52 and input to voltage-to-frequency converter 54, as described above.

The operation of this preferred embodiment is dependent on the difference in impedance that generally exists between the blood and solid substances that make up stenoses. While blood is a liquid electrolyte solution having generally low impedance, stenoses typically comprise solidified lipids having high impedance. Referring to FIG. 1A, it will thus be appreciated that the impedance measured across blood vessel 20 along axis 62, passing through stenosis 22, will be significantly higher than that measured along axis 64, where the vessel or stent is clear of stenoses. Similarly, if a stenosis has accumulated within stent 24 in between electrodes 28 and 30, the impedance measured between the electrodes (i.e., the potential measured between the electrodes for a given current) will increase, relative to earlier measurements. Such an impedance increase can be taken to indicate that flow through the stent has been constricted. If the degree of constriction is known, based on the impedance increase, it can be used to correct calculations of flow volume through the stent to account for the constriction.

Additional pairs of electrodes may be placed at different axial positions along the length of stent 24, so as to measure impedance and thus detect relative flow constriction at each of the positions. Such relative constriction measurements are particularly useful in follow-up evaluation of arterial bypass and other blood vessel grafts.

Stent 24 may further include other sensors, of other types known in the art, for example, pressure sensors, as will be described in greater detail below, pH and other chemical sensors, temperature sensors and oxygen saturation sensors. Preferably, these sensors are fabricated on or in the stent using silicon microcircuit technology and are integrated with circuitry 26, so that signals from the sensors are transmitted by coil 40 to receiver 48 along with the flow-related signals.

In the preferred embodiments illustrated by FIGS. 3, 4A and 4B, circuitry 26 receives electrical power only from external transmitter 47. Stent 24 includes no power source of its own, and circuitry 26 is inactive except when in a vicinity of operating transmitter 47.

In other preferred embodiments of the present invention, however, electrical power is supplied to circuitry 26 by a battery. The battery is preferably built into stent 24, and more preferably is contained within modulator 36. In this case, circuitry 26 can provide a continuous reading of flow through the stent, by measurement of bioimpedance, for example, as described above, or by means of other measurement methods to be described below. Alternatively, circuitry 26 may read the flow intermittently in single measurements or short bursts, preferably at regular intervals or alternatively, triggered by an outside signal applied to the circuitry. This autonomous-reading stent is preferably used in conjunction with a receiver on or adjacent to the subject's body so as to provide a continuous or intermittent record of flow through the stent, as well as other parameters measured by additional sensors, as described above. It may be particularly useful in monitoring the subject's status during the period immediately following stent implantation, for a time as long as the useful life of the battery.

Figure 5A:
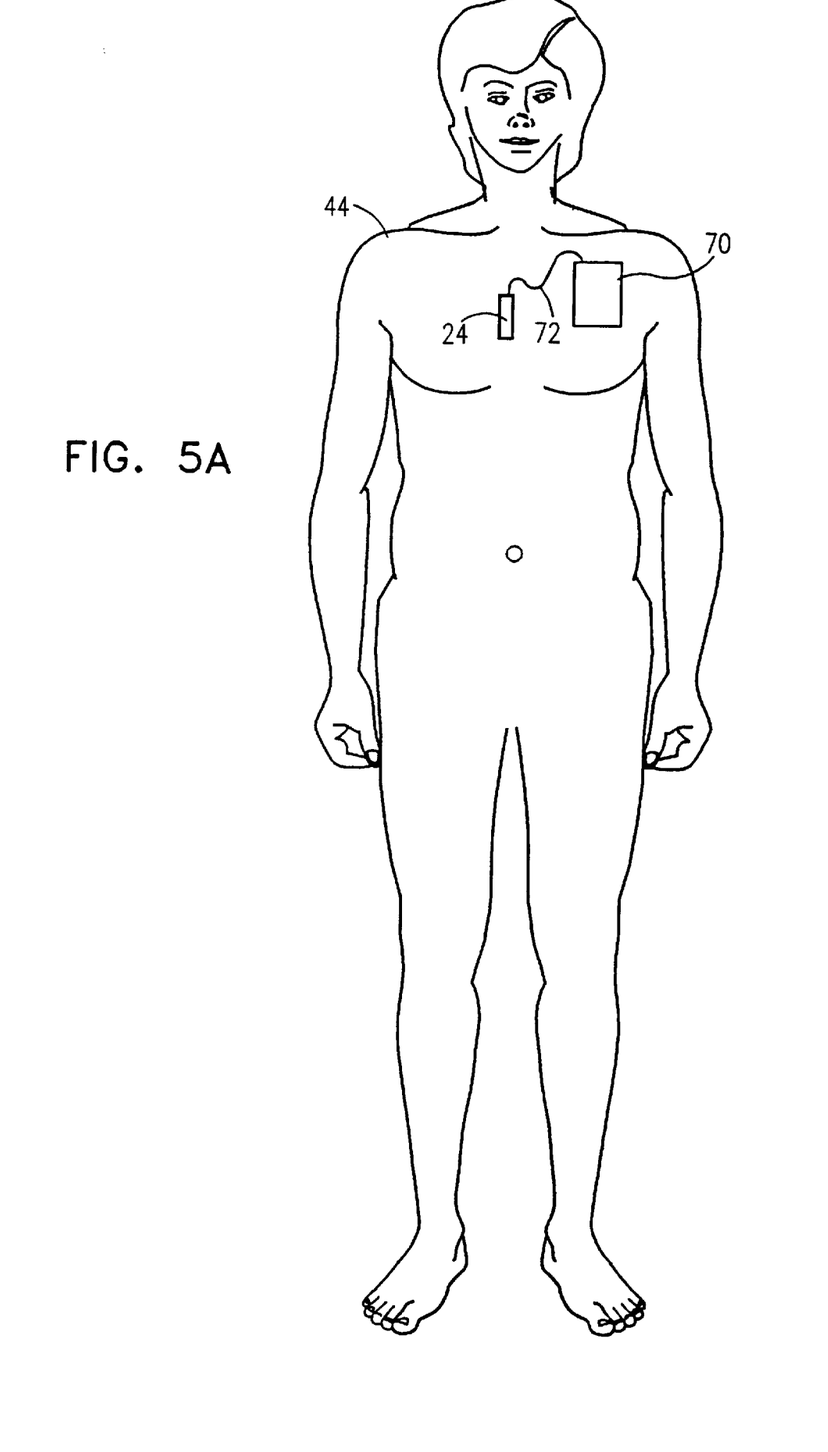
FIG. 5A is a schematic illustration showing a battery-powered stent and an accompanying capsule, implanted in the body of a subject, in accordance with a preferred embodiment of the present invention.

FIG. 5A illustrates schematically an alternative preferred embodiment of the present invention, wherein the battery is contained in a separate compartment, preferably in a capsule 70 implanted under the skin of subject 44, similar to capsules known in the art for use in conjunction with cardiac pacemakers, for example. Capsule 70 is connected by wires 72 to stent 24.

Figure 5B:
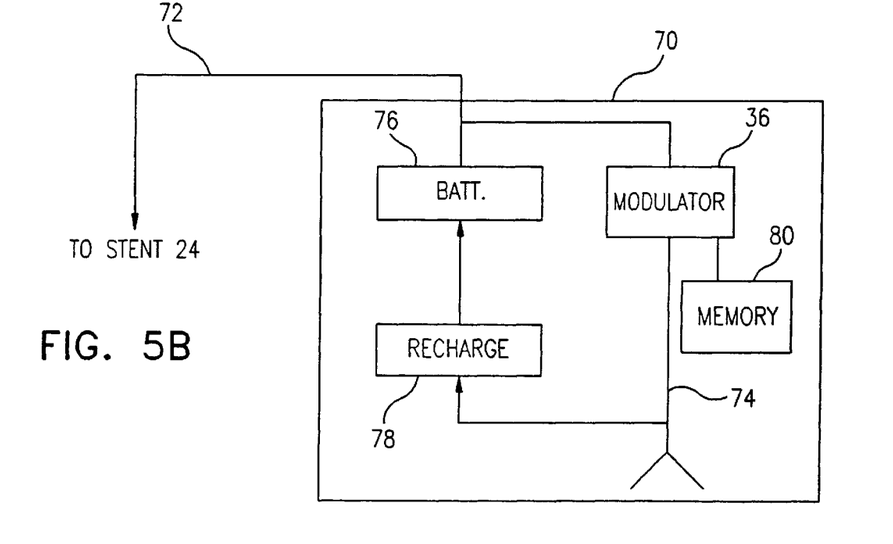
FIG. 5B is a schematic illustration of the capsule of FIG. 5A, showing circuitry contained within the capsule, in accordance with a preferred embodiment of the present invention.

FIG. 5B is a schematic illustration showing elements contained in capsule 70, in accordance with a preferred embodiment of the present invention. Capsule 70 contains all or a portion of the elements of modulator 36, as well as an antenna 74 for transmitting signals to a receiver outside the body, such as receiver 48, in place of coil 40. The battery is preferably a rechargeable battery 76, and the capsule includes inductive recharging circuitry 78, as is known in the art. Battery 76 is recharged by application of an external electromagnetic field to capsule 70, from which-energy is received by antenna 74 and is rectified and supplied to the battery by circuitry 78.

Capsule 70 may further include memory 80, coupled to modulator 36, for receiving and storing data regarding blood flow through stent 24 and other parameters. Memory 80 preferably preserves a continuous record of the data, which record is then transmitted to the receiver outside the body upon command. It will be understood that battery 76 is connected to provide electrical power to modulator 36 and memory 80, as well as to stent 24, although these connections are not shown in FIG. 5B for the sake of simplicity of illustration.

In the preferred embodiments described above, blood flow through stent 24 is measured by sensing electrical characteristics related to the flow. In other preferred embodiments of the present invention, however, the flow sensing function of the stent is accomplished by measuring other flow-related parameters, such as fluid pressure. In accordance with well-known principles of fluid dynamics, upstream of an occlusion in a blood vessel, the pressure will be high. In the area of the occlusion and downstream therefrom, the pressure decreases. Pressure variations may thus be used as indicators of corresponding variations in flow rate.

It will be appreciated that pressure within a blood vessel, and particularly within an artery, is generally not constant, but rather varies in pulsatile fashion, driven by the beating of the heart. Therefore, wherever pressure measurements or pressure comparisons are described in the context of the present patent application, they will be generally understood to refer to measurements or comparisons of systolic (peak) pressure or, preferably, of the difference between systolic and diastolic pressures at a given location along the blood vessel or stent. In some preferred embodiments of the present invention, however, pressure measurements are made at higher sampling rates, for example, at intervals of a few milliseconds, so that pressure waveforms may be derived and compared.

Figure 6:
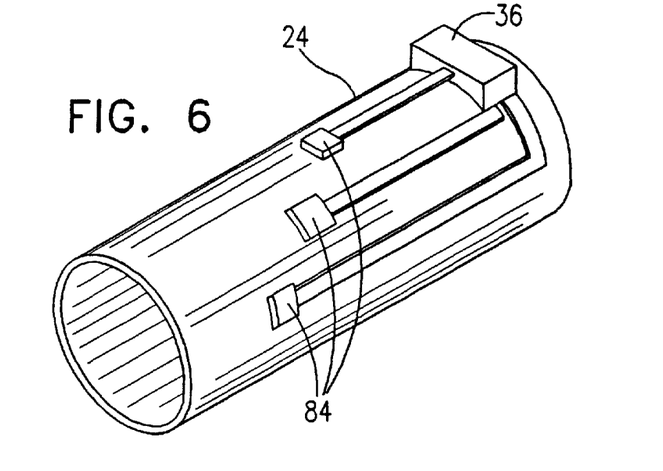
FIG. 6 is a schematic illustration of a stent including a plurality of pressure sensors, in accordance with a preferred embodiment of the present invention.

FIG. 6 is a schematic illustration showing stent 24 in accordance with a preferred embodiment of the present invention based on pressure measurement. A plurality of pressure sensors 84 are placed at different axial positions along the length of the stent, so as to measure the pressure at each of the positions. Variations in pressure from one sensor to another, or variations over time in the difference between systolic and diastolic pressures at one or more of the sensors, may generally be indicative of the development and growth of occlusions in lumen 34 of stent 24.

Sensors 84 are coupled to modulator 36, and the pressure measurements made by the sensors are transmitted to a receiver outside the body, as described herein with regard to other preferred embodiments. Sensors 84 may comprise any suitable type of pressure sensors known in the art, for example, piezoelectric sensors or, alternatively, micromachined silicon strain gages, such as produced by Lucas Novasensor of Fremont, Calif.

Figure 7A:
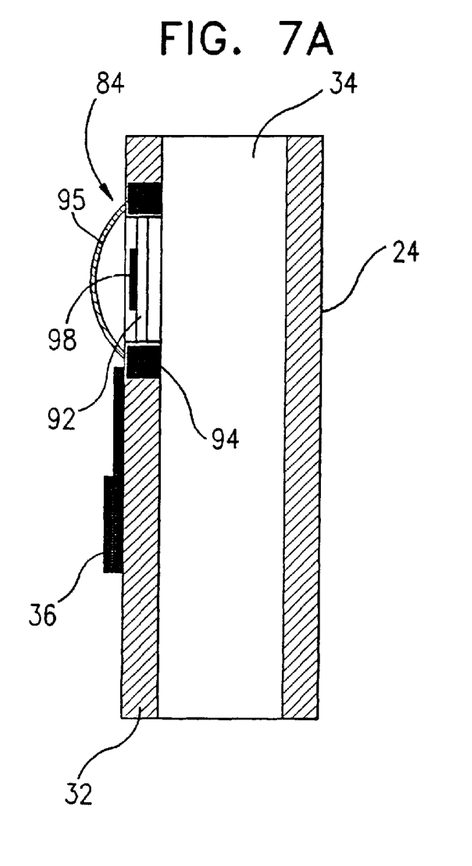
FIGS. 7A and 7B are schematic, sectional illustrations showing a pressure sensor comprising a flexible diaphragm within the wall of a stent, in accordance with a preferred embodiment of the present invention, in low-pressure (FIG. 7A) and high-pressure (FIG. 7B) positions.
Figure 7B:
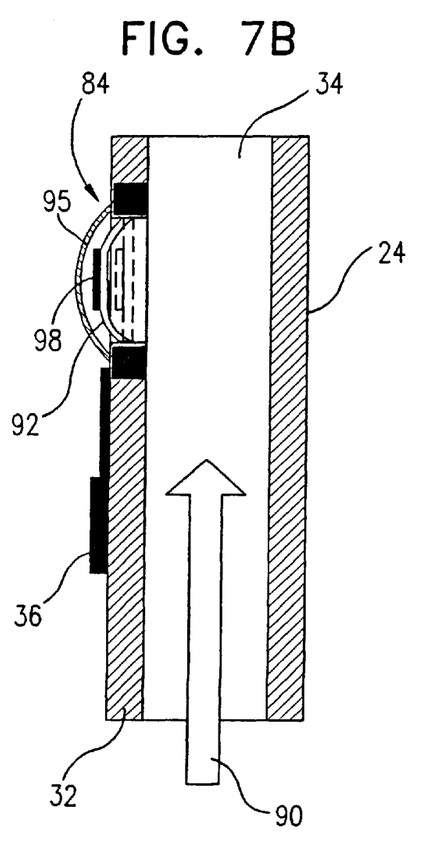

FIGS. 7A and 7B schematically illustrate, in sectional view, a portion of stent 24 in accordance with a preferred embodiment of the present invention in which pressure sensor 84 comprises a moving diaphragm-type sensor. Multiple sensors of this type may preferably be placed along the length of stent 24, as described above. FIG. 7A shows sensor 84 during diastole, at relatively low pressure inside lumen 34, and FIG. 7B shows the sensor during systole, at increased pressure and flow rate, as indicated schematically by arrow 90.

Sensor 84 comprises a flexible diaphragm 92, comprising, for example, silicone rubber or other biocompatible, resilient material known in the art, fixed within wall 32 of stent 24. Diaphragm 92 is surrounded circumferentially by an inductance coil 94, which is electrically coupled to elements of modulator 36 to form a resonant circuit having a characteristic frequency dependent on the inductance of the coil, as will be described below. A ferrite core 98 is fixed to diaphragm 92, within coil 94. All the elements of sensor 84 and associated circuitry are preferably fabricated on or within wall 32 using methods of microcircuit and/or thin film technology known in the art. A cap 95 preferably covers the elements of sensor 84 and ensures that diaphragm 92 may expand outward without encountering resistance from the blood vessel in which stent 24 is implanted.

As shown in FIG. 7B, during systole, diaphragm 92 expands radially outwards with respect to wall 32, thus displacing ferrite 98 relative to coil 94 by a distance proportional to the pressure increase. This displacement causes a proportional change in the inductance of the coil, which alters the characteristic frequency of the resonant circuit. A receiver outside the body of the subject, such as receiver 48 (shown in FIG. 3), receives signals transmitted by stent 24 and analyzes frequency changes in the signals, in order to measure the pressure change at sensor 84.

Alternatively, a strain gauge, as is known in the art, may be mounted on diaphragm 92, so as to generate signals responsive to the displacement of the diaphragm.

Figure 8:
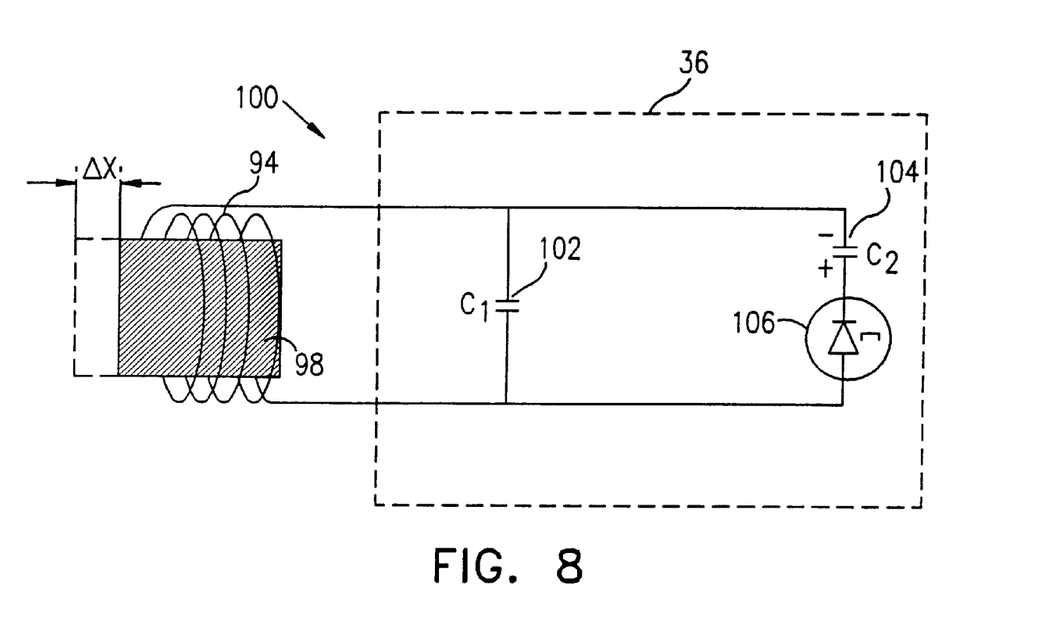
FIG. 8 is a schematic electrical circuit diagram, illustrating a sensor and transceiver circuit for use in conjunction with the pressure sensor of FIGS. 7A and 7B, in accordance with a preferred embodiment of the present invention.

FIG. 8 is a schematic diagram illustrating a resonant oscillator circuit 100 including coil 94 and elements of modulator 36, for use in conjunction with sensor 84 shown in FIGS. 7A and 7B, in accordance with a preferred embodiment of the present invention. Circuit 100 is a tunnel diode oscillator circuit, as is known in the art, and comprises, in addition to coil 94, capacitors 102 and 104 and a tunnel diode 106, suitably biased so as to operate in a negative resistance regime, as is known in the art. Capacitors 102 and 104 have respective capacitances $C_1$ and $C_2$, wherein $C_1 \cong 0.1$ μF, and $C_2 \cong 0.1$ μF. Coil 94 preferably includes 10–30 turns of diameter 1 mm, so that its baseline inductance $L_0$ (assuming ferrite core 98 to be centered in the coil) is approximately 2–3 μH.

In the absence of displacement of ferrite 98, circuit 100 oscillates at a baseline resonant frequency $f_0$ given generally by:

$$f_0 \cong \frac{1}{2\pi}\sqrt{\frac{1}{L_0 C}} \quad (1)$$

wherein C is the total capacitance of the circuit. Coil 94 radiates at this frequency. When the pressure in lumen 34 increases, as shown in FIG. 7B, ferrite 98 will be displaced by a distance ΔX, as described above, and the inductance will consequently change by an proportional amount ΔL. As a result, the resonant frequency of circuit 100, at which coil 94 radiates, will vary by an increment Δf, given approximately by:

$$\Delta f \cong \frac{1}{2} C \Delta L f_0 \quad (2)$$

Figure 9:
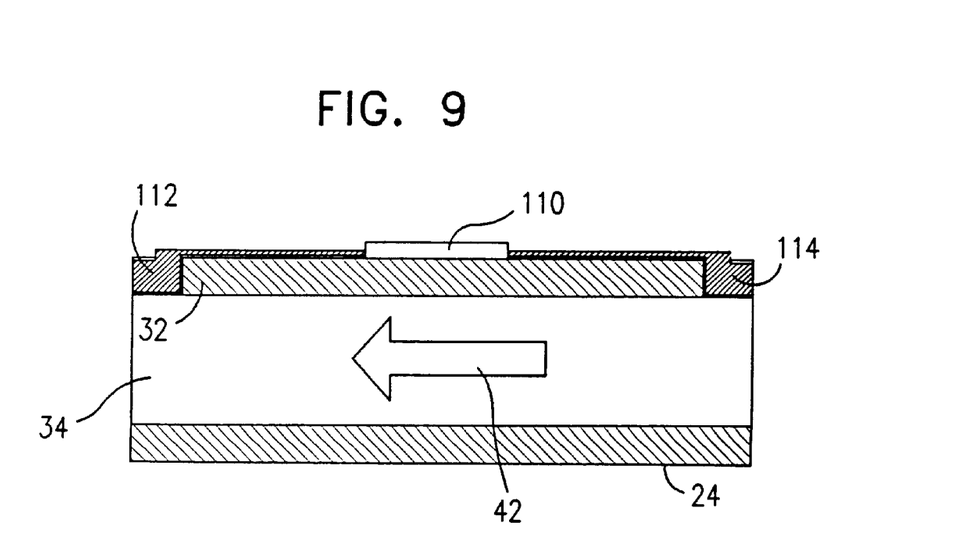
FIG. 9 is a schematic illustration of a stent including ultrasound-responsive devices for use in ultrasonic measurement of blood flow through the stent, in accordance with a preferred embodiment of the present invention.

FIG. 9 schematically illustrates, in sectional view, still another preferred embodiment of the present invention, in which stent 24 includes ultrasound transducers 112 and 114 at respective downstream and upstream ends of the stent, for use in measuring the rate of blood flow through lumen 34. Preferably, transducers 112 and 114 are contained within wall 32 of stent 24, in communication with the lumen. Alternatively, transducers 112 and 114 may be separate from stent 24 and held in place at respective positions along a blood vessel in which the stent is implanted, each of the transducers at a known distance from its respective end of the stent.

Further preferably, as shown in FIG. 9, transducers 112 and 114 are coupled to circuitry 110, which serves some or all of the functions of receiving energy from an external source, as described above, driving the transducers, receiving flow-responsive signals from the transducers, and transmitting the signals to an external receiver.

In one preferred embodiment of the present invention, circuitry 110 and transducers 112 and 114 function as a transit-time flow meter. Circuitry 110 drives downstream transducer 112 to emit ultrasonic waves into lumen 34. These waves are received by upstream transducer 114, after an upstream transit time dependent on the (fixed) distance between the two transducers and the velocity of blood flow through the lumen. Similarly, transducer 114 is driven to emit and transducer 112 receives, after a downstream transit time, ultrasonic waves. The difference between the longer upstream and the shorter downstream transit times is indicative of the blood flow velocity in lumen 34.

In another preferred embodiment of the present invention, circuitry 110 and at least one of transducers 112 and 114 unction as a Doppler ultrasound flow meter. Preferably, the at least one of transducers 112 and 114 is aimed inward, into lumen 34, so as to emit and receive ultrasonic waves primarily along respective radiation axes at predetermined, acute angles to the longitudinal axis of stent 24. The Doppler frequency shift of the waves received by the at least one of the transducers is indicative of the blood flow velocity in the lumen adjacent to the transducer.

Preferably, measurements of blood flow velocity, in accordance with preferred embodiments of the present invention illustrated by FIG. 9, are repeated periodically over an extended period of time. Increased flow velocity measured by one of the transducers 112 or 114 will generally indicate that there is an occlusion developing in the stent or the blood vessel upstream of the transducer, whereas decreased flow velocity may indicate an occlusion developing downstream. Any significant difference between the velocities measured by transducers 112 and 114 will generally be indicative of an occlusion developing within stent 24.

In still another preferred embodiment of the present invention, the Doppler ultrasound measurement of blood flow velocity in and near stent 24 is made using an external Doppler ultrasound system, preferably a Doppler imaging system, as is known in the art. Operation of such systems is frequently hampered by the difficulty of aligning and maintaining alignment of an external ultrasound probe, associated with the Doppler system, with the stent and/or blood vessel of interest. Furthermore, frequently inaccuracy is introduced in the Doppler measurements of blood flow velocity, due to uncertainty as to the angle of the probe relative to the axis of the stent.

Therefore, in this preferred embodiment, transducers 112 and 114 function as ultrasonic transponders, thus serving as fiduciary marks so that a user of the external Doppler system can locate exactly the ends of stent 24 and determine the probe's angle relative to the stent axis. The fiduciary marks enable the user to align the probe for optimal signal/noise ratio and to maintain proper alignment even if the subject or his internal organs shift during measurement. Preferably, the transponders operate as frequency doublers, as are known in the art, so as to mark the ends of the stent more clearly. Alternatively, the transponders may be replaced by other types of ultrasound markers, such as hollow bubbles, that give sharp peak reflections, as are known in the art.

It will further be appreciated, based on the preferred embodiments described above, that stents in accordance with the present invention may advantageously used for both short-term, generally continuous monitoring and long-term, intermittent monitoring of flow through the stent. In short-term monitoring, flow-responsive signals may be received from the stent to observe changes in blood flow during exercise, for example. In long-term monitoring, successive measurements over a period of time may be stored and compared, in order to follow changes in an occlusion upstream, downstream or within the stent.

It will also be understood that the preferred embodiments described above are cited by way of example, and the full scope of the invention is limited only by the claims.

What is claimed is:

1. Implantable apparatus for measuring a fluid flow in the body of a subject, comprising:
    a stent, having a generally cylindrical radial outer wall and a central lumen;
    a flow parameter sensor fixed to the stent, which measures a parameter relating to a rate of blood flow through the stent; and
    a transmitter, which transmits signals responsive to the measured parameter to a receiver outside the body; and
    wherein the transmitter comprises a coil fixed to the stent.

2. Apparatus according to claim 1, wherein the flow parameter sensor comprises a pair of electrodes, in communication with the lumen.

3. Apparatus according to claim 1, wherein the flow parameter sensor measures a magnetohydrodynamic potential across the lumen.

4. Apparatus according to claim 1, wherein the flow parameter sensor measures an electrical impedance across the lumen.

5. Apparatus according to claim 1, wherein the flow parameter sensor comprises at least one pressure sensor.

6. Apparatus according to claim 5, wherein the pressure sensor comprises a pressure-to-frequency transducer.

7. Apparatus according to claim 1, wherein the flow parameter sensor comprises at least one ultrasound-responsive device.

8. Apparatus according to claim 1, wherein the coil is helically-disposed within the outer wall of the stent, along the length thereof.

9. Implantable apparatus for measuring a fluid flow in the body of a subject, comprising:
    a stent, having a generally cylindrical radial outer wall and a central lumen;
    a flow parameter sensor fixed to the stent, which measures a parameter relating to a rate of blood flow through the stent;
    a transmitter, which transmits signals responsive to the measured parameter to a receiver outside the body; and
    wherein the flow parameter sensor comprises:
        a flexible diaphragm, fixed within the outer wall of the stent so as to expand radially outward in response to a pressure increase in the lumen; and
        a deflection sensor, which generates signals responsive to expansion of the diaphragm.

10. Apparatus according to claim 9, wherein the deflection sensor comprises:
    a magnetic core fixed to the diaphragm; and
    an electrical coil, circumferentially surrounding the diaphragm and the coil, so that movement of the core due to expansion of the diaphragm causes a change in the inductance of the coil, responsive to the pressure increase.

11. Implantable apparatus for measuring a fluid flow in the body of a subject, comprising:
    a stent, having a generally cylindrical radial outer wall and a central lumen;
    a flow parameter sensor fixed to the stent, which measures a parameter relating to a rate of blood flow through the stent;
    a transmitter, which transmits signals responsive to the measured parameter to a receiver outside the body; and
    wherein the transmitter comprises:
        the electrical coil; and
        circuitry coupled to the coil, having a resonant frequency dependent on the inductance of the coil,
        circuitry coupled to the coil, having a resonant frequency dependent on the inductance of the coil,
    wherein the coil receives energy from an electromagnetic field and radiates energy substantially at the resonant frequency.

12. Implantable apparatus for measuring a fluid flow in the body of a subject, comprising:
    a stent, having a generally cylindrical radial outer wall and a central lumen;
    a flow parameter sensor fixed to the stent, which measures a parameter relating to a rate of blood flow through the stent; and
    a transmitter, which transmits signals responsive to the measured parameter to a receiver outside the body; and
    comprising an implantable capsule, which supplies energy to the flow parameter sensor.

13. A method for measuring blood flow in the body of a subject, comprising:
    implanting a stent, to which a transmitter is coupled, in a blood vessel in the body;
    receiving signals from the transmitter, responsive to blood flow through the stent; and
    comprising irradiating the body with an electromagnetic field, to provide energy to the stent.

14. A method for measuring blood flow in the body of a subject, comprising:
    implanting a stent, to which a transmitter is coupled, in a blood vessel in the body;
    receiving signals from the transmitter, responsive to blood flow through the stent; and
    comprising receiving an ECG signal from the subject, and using the ECG signal in analyzing the blood flow signals received from the transmitter.

15. A method for measuring blood flow in the body of a subject, comprising:
    implanting a stent, to which a transmitter is coupled, in a blood vessel in the body;
    receiving signals from the transmitter, responsive to blood flow through the stent; and
    comprising:
        applying a magnetic field to the body in a vicinity of the stent, in a direction generally transverse to the flow of blood through the stent; and
        measuring an electrical potential across the stent, along a transverse axis thereof generally perpendicular to the direction of the magnetic field,
    wherein receiving signals from the transmitter comprises receiving signals responsive to the electrical potential.

16. A method for measuring blood flow in the body of a subject, comprising:
    implanting a stent, to which a transmitter is coupled, in a blood vessel in the body;
    receiving signals from the transmitter, responsive to blood flow through the stent; and
    comprising measuring a bioimpedance across the stent, wherein receiving signals from the transmitter comprises receiving signals responsive to the bioimpedance.

17. A method for measuring blood flow in the body of a subject, comprising:
   implanting a stent, to which a transmitter is coupled, in a blood vessel in the body;
   receiving signals from the transmitter, responsive to blood flow through the stent; and
   comprising measuring a pressure in the stent, wherein receiving signals from the transmitter comprises receiving signals responsive to the pressure.

18. A method for measuring blood flow in the body of a subject, comprising:
   implanting a stent, to which a transmitter is coupled, in a blood vessel in the body;
   receiving signals from the transmitter, responsive to blood flow through the stent; and
   comprising detecting ultrasonic signals from blood flowing in the stent, wherein receiving signals from the transmitter comprises receiving signals responsive to the detected ultrasonic signals.

19. A method for measuring blood flow in a stent implanted in a blood vessel in the body of a subject, comprising:
   implanting two ultrasound markers along the blood vessel, each marker in a known spatial relation to a respective end of the stent;
   determining respective positions of the markers relative to an ultrasound probe;
   aligning the probe with a long axis of the stent using the determined positions of the markers; and
   receiving and analyzing Doppler ultrasound signals from blood flowing in the stent.

20. A method according to any of claims 19, wherein determining the positions of the markers comprises forming an ultrasound image of a portion of the body that contains the stent.

21. A method for fabricating a stent, comprising:
   forming at least a portion of the stent from non-conducting material;
   fixing electronic components to the portion; and
   printing strips of conducting material on a surface of the portion to interconnect the components.

22. A method according to claim 21, wherein forming the device from non-conducting material comprises forming the device from polyimide plastic.

23. A method according to claim 21, wherein printing the strips on the surface comprises transferring an image of the strips to the surface by photolithography.

24. A stent, at least a portion of which comprises non-conducting material, and comprising:
   a plurality of electronic components fixed to the portion; and
   one or more strips of conducting material printed on a surface of the portion to interconnect the components.

* * * * *